(12) United States Patent
Pickett et al.

(10) Patent No.: US 10,014,452 B2
(45) Date of Patent: Jul. 3, 2018

(54) SEMICONDUCTOR NANOPARTICLE-BASED LIGHT-EMITTING DEVICES AND ASSOCIATED MATERIALS AND METHODS

(71) Applicant: Nanoco Technologies Ltd., Manchester (GB)

(72) Inventors: Nigel Pickett, Manchester (GB); James Harris, Manchester (GB)

(73) Assignee: Nanoco Technologies Ltd., Manchester (GB)

( * ) Notice: Subject to any disclaimer, the term of this patent is extended or adjusted under 35 U.S.C. 154(b) by 0 days.

(21) Appl. No.: 15/241,328

(22) Filed: Aug. 19, 2016

(65) Prior Publication Data

US 2016/0359093 A1 Dec. 8, 2016

Related U.S. Application Data

(62) Division of application No. 14/584,893, filed on Dec. 29, 2014, now Pat. No. 9,461,215, which is a division (Continued)

(30) Foreign Application Priority Data

Nov. 19, 2008 (GB) .................................. 0821122.9

(51) Int. Cl.
*H01L 33/56* (2010.01)
*B82Y 15/00* (2011.01)
(Continued)

(52) U.S. Cl.
CPC ............... *H01L 33/56* (2013.01); *B82Y 15/00* (2013.01); *C09K 11/02* (2013.01); *C09K 11/565* (2013.01);
(Continued)

(58) Field of Classification Search
CPC ......... H01L 33/56; H01L 33/00; H01L 33/04; H01L 33/50; H01L 33/005; H01L 33/502;
(Continued)

(56) References Cited

U.S. PATENT DOCUMENTS 9,461,215 B2 10/2016 Pickett et al.
2003/0148544 A1 8/2003 Nie et al.
(Continued)

FOREIGN PATENT DOCUMENTS

JP   2007173755 A   7/2007

OTHER PUBLICATIONS

European Search Report received in corresponding European patent application No. 09 774 6903 1564 dated Jan. 24, 2017.
(Continued)

*Primary Examiner* — Chuong A Luu
(74) *Attorney, Agent, or Firm* — Blank Rome, LLP

(57) ABSTRACT

Embodiments of the present invention relate to a formulation for use in the fabrication of a light-emitting device, the formulation including a population of semiconductor nanoparticles incorporated into a plurality of discrete microbeads comprising an optically transparent medium, the nanoparticle-containing medium being embedded in a host light-emitting diode encapsulation medium. A method of preparing such a formulation is described. There is further provided a light-emitting device including a primary light source in optical communication with such a formulation and a method of fabricating the same.

12 Claims, 6 Drawing Sheets

Related U.S. Application Data of application No. 12/622,012, filed on Nov. 19, 2009, now Pat. No. 8,921,827.

(60) Provisional application No. 61/116,142, filed on Nov. 19, 2008, provisional application No. 61/116,516, filed on Nov. 20, 2008.

(51) Int. Cl.
| | |
|---|---|
| *C09K 11/02* | (2006.01) |
| *C09K 11/56* | (2006.01) |
| *C09K 11/70* | (2006.01) |
| *C09K 11/88* | (2006.01) |
| *G01N 33/58* | (2006.01) |
| *H01L 33/00* | (2010.01) |
| *H01L 33/04* | (2010.01) |
| *H01L 33/50* | (2010.01) |

(52) U.S. Cl.
CPC ............ *C09K 11/70* (2013.01); *C09K 11/883* (2013.01); *G01N 33/588* (2013.01); *H01L 33/005* (2013.01); *H01L 33/04* (2013.01); *H01L 33/502* (2013.01); *H01L 33/501* (2013.01); *H01L 2224/48091* (2013.01); *H01L 2924/181* (2013.01); *H01L 2933/005* (2013.01); *H01L 2933/0041* (2013.01)

(58) Field of Classification Search
CPC ......... H01L 33/504; H01L 2224/48091; H01L 2933/005; H01L 2933/0041
USPC .......................................................... 257/98
See application file for complete search history.

(56) References Cited

U.S. PATENT DOCUMENTS

| | | |
|---|---|---|
| 2006/0019098 A1 | 1/2006 | Chan et al. |
| 2006/0068154 A1 | 3/2006 | Parce et al. |
| 2006/0157686 A1 | 7/2006 | Jang et al. |
| 2007/0199109 A1* | 8/2007 | YI ............................. B22F 1/02 |
| | | 428/332 |
| 2007/0238126 A1* | 10/2007 | Pickett ................. G01N 33/585 |
| | | 435/6.12 |
| 2008/0230750 A1* | 9/2008 | Gillies ................... B82Y 30/00 |
| | | 252/500 |
| 2011/0133237 A1 | 6/2011 | Koike et al. |

OTHER PUBLICATIONS

English translation of Korean Office Action received in corresponding Korean patent application No. 10-2016-7027486.

\* cited by examiner

SEMICONDUCTOR NANOPARTICLE-BASED LIGHT-EMITTING DEVICES AND ASSOCIATED MATERIALS AND METHODS

RELATED APPLICATIONS

This application is a division of U.S. patent application Ser. No. 14/584,893 filed Dec. 29, 2014 now U.S. Pat. No. 9,461,215, which is a division of U.S. patent application Ser. No. 12/622,012 filed Nov. 19, 2009, now U.S. Pat. No. 8,921,827, which claims the benefit of U.S. Provisional Patent Application No. 61/116,142 filed Nov. 19, 2008, U.S. Provisional Patent Application No. 61/116,516 filed Nov. 20, 2008, and U.K. Patent Application GB 0821122.9 filed Nov. 19, 2008, the disclosures of which are hereby incorporated by reference in their entireties.

FIELD OF THE INVENTION

The present invention relates to semiconductor nanoparticle—based light-emitting devices and associated materials and methods. Particularly, but not exclusively, the present invention relates to formulations for use in the fabrication of quantum dot based light-emitting devices and methods for producing such devices employing such formulations.

BACKGROUND

Light-emitting diodes (LEDs) are becoming more important to modern day life and it is envisaged that they will become one of the major applications in many forms of lighting such as automobile lights, traffic signals, general lighting, liquid crystal display (LCD) backlighting and display screens. Currently, LED devices are typically made from inorganic solid-state compound semiconductors, such as AlGaAs (red), AlGaInP (orange-yellow-green), and AlGaInN (green-blue). However, using a mixture of the available solid-state compound semiconductors, solid-state LEDs that emit white light cannot be produced. Moreover, it is difficult to produce "pure" colors by mixing solid-state LEDs of different frequencies. Therefore, currently the main method of color mixing to produce a required color, including white, is to use a combination of phosphorescent materials that are placed on top of the solid-state LED whereby the light from the LED (the "primary light") is absorbed by the phosphorescent material and then re-emitted at a different frequency (the "secondary light"), i.e., the phosphorescent materials down convert the primary light to the secondary light. Moreover, the use of white LEDs produced by phosphor down-conversion leads to lower cost and simpler device fabrication than a combination of solid-state red-green-blue LEDs.

Current phosphorescent materials used in down converting applications absorb UV or mainly blue light and convert it to longer wavelengths, with most phosphors currently using trivalent rare-earth doped oxides or halophosphates. White emission can be obtained by blending phosphors that emit in the blue, green and red regions with that of a blue or UV emitting solid-state device. i.e., a blue light-emitting LED plus a green phosphor such as, $SrGa_2S_4:Eu_2^+$, and a red phosphor such as, $SrSiEu_2^+$ or a UV light-emitting LED plus a yellow phosphor such as, $Sr_2P_2O_7:Eu_2^+;Mu_2^+$, and a blue-green phosphor. White LEDs can also be made by combining a blue LED with a yellow phosphor, however, color control and color rendering may be poor when using this methodology due to lack of tunability of the LEDs and the phosphor. Moreover, conventional LED phosphor technology uses down converting materials that have poor color rendering (i.e., color rendering index (CRI)<75).

SUMMARY

There has been substantial interest in exploiting the properties of compound semiconductors consisting of particles with dimensions in the order of 2-50 nm, often referred to as quantum dots (ODs) or nanocrystals. These materials are of commercial interest due to their size-tuneable electronic properties that can be exploited in many commercial applications such as optical and electronic devices and other applications, including biological labelling, photovoltaics, catalysis, biological imaging, LEDs, general space lighting and electroluminescent displays, amongst many new and emerging applications.

The most studied of semiconductor materials have been the chalcogenides II-VI materials namely ZnS, ZnSe, CdS, CdSe, CdTe; most noticeably CdSe due to its tuneability over the visible region of the spectrum. Reproducible methods for the large scale production of these materials have been developed from "bottom up" techniques, whereby particles are prepared atom-by-atom, i.e., from molecules to clusters to particles, using "wet" chemical procedures.

Two fundamental factors, both related to the size of the individual semiconductor nanoparticle, are responsible for their unique properties. The first is the large surface-to-volume ratio; as a particle becomes smaller, the ratio of the number of surface atoms to those in the interior increases. This leads to the surface properties playing an important role in the overall properties of the material. The second factor is, with many materials including semiconductor nanoparticles, that there is a change in the electronic properties of the material with size, moreover, because of quantum confinement effects the band gap gradually becomes larger as the size of the particle decreases. This effect is a consequence of the confinement of an electron in a box giving rise to discrete energy levels similar to those observed in atoms and molecules, rather than a continuous band as observed in the corresponding bulk semiconductor material. Thus, for a semiconductor nanoparticle, because of the physical parameters, the "electron and hole", produced by the absorption of electromagnetic radiation, a photon, with energy greater than the first excitonic transition, are closer together than they would be in the corresponding macrocrystalline material. Moreover, the Coulombic interaction cannot be neglected. This leads to a narrow bandwidth emission that depends upon the particle size and composition of the nanoparticle material. Thus, quantum dots have higher kinetic energy than the corresponding macrocrystalline material and consequently the first excitonic transition (band gap) increases in energy with decreasing particle diameter.

Core semiconductor nanoparticles that consist of a single semiconductor material along with an outer organic passivating layer tend to have relatively low quantum efficiencies due to electron-hole recombination occurring at defects and dangling bonds situated on the nanoparticle surface that may lead to non-radiative electron-hole recombinations. One method to eliminate defects and dangling bonds on the inorganic surface of the quantum dot is to grow a second inorganic material, having a wider band-gap and small lattice mismatch to that of the core material epitaxially on the surface of the core particle, to produce a "core-shell" particle. Core-shell particles separate any carriers confined in the core from surface states that would otherwise act as non-radiative recombination centres. One example is a ZnS shell grown on the surface of a CdSe core. Another approach is to prepare a core-multi shell structure where the "electron-hole" pair is completely confined to a single shell layer consisting of a few monolayers of a specific material such as a quantum dot-quantum well structure. Here, the core is of a wide band gap material, followed by a thin shell of narrower band gap material, and capped with a further wide band gap layer, such as CdS/HgS/CdS grown using substitution of Hg for Cd on the surface of the core nanocrystal to deposit just a few monolayers of HgS that is then over grown by a monolayer of CdS. The resulting structures exhibit clear confinement of photo-excited carriers in the HgS layer. To add further stability to quantum dots and help to confine the electron-hole pair one of the most common approaches is to epitaxially grow a compositionally graded alloy layer on the core. This can help to alleviate strain that could otherwise lead to defects. Moreover, for a CdSe core, in order to improve structural stability and quantum yield, rather than growing a shell of ZnS directly on the core a graded alloy layer of $Cd_{1-x}Zn_xSe_{1-y}S_y$ can be used. This has been found to greatly enhance the photoluminescence emission of the quantum dots.

Doping quantum dots with atomic impurities is an efficient way also of manipulating the emission and absorption properties of the nanoparticle. Procedures for doping of wide band gap materials, such as zinc selenide and zinc sulfide, with manganese and copper (ZnSe:Mn or ZnS:Cu), have been developed. Doping with different luminescence activators in a semiconducting nanocrystal can tune the photoluminescence and electroluminescence at energies even lower than the band gap of the bulk material whereas the quantum size effect can tune the excitation energy with the size of the quantum dots without having a significant change in the energy of the activator related emission.

Rudimentary quantum dot-based light-emitting devices have been made by embedding colloidally produced quantum dots in an optically clear LED encapsulation medium, typically a silicone or an acrylate, that is then placed on top of a solid-state LED. The use of quantum dots potentially has some significant advantages over the use of the more conventional phosphors, such as the ability to tune the emission wavelength, strong absorption properties, and low scattering if the quantum dots are mono-dispersed.

For the commercial application of quantum dots in next-generation light-emitting devices, the quantum dots are preferably incorporated into the LED encapsulating material while remaining as fully mono-dispersed as possible and without significant loss of quantum efficiency. The methods developed to date are problematic, not least because of the nature of current LED encapsulants. Quantum dots can agglomerate when formulated into current LED encapsulants thereby reducing the optical performance of the quantum dots. Moreover, once the quantum dots are incorporated into the LED encapsulant, oxygen can migrate through the encapsulant to the surfaces of the quantum dots, which can lead to photo-oxidation and, as a result, a drop in quantum yield (QY). Although reasonably efficient quantum dot-based light-emitting devices can be fabricated under laboratory conditions building on current published methods, there remain significant challenges to develop materials and methods for fabricating quantum dot-based light-emitting devices under commercial conditions on an economically viable scale.

In some embodiments, the present invention may obviate or mitigate one or more of the problems with current methods for fabricating semiconductor nanoparticle-based light-emitting devices.

Embodiments of the present invention may feature a formulation for use in the fabrication of a light-emitting device. The formulation may include a population of semiconductor nanoparticles incorporated into a plurality of discrete microbeads comprising an optically transparent medium, the nanoparticle-containing medium being embedded in a host light-emitting diode (LED) encapsulation medium.

One or more of the following features may be included. Each of the discrete microbeads may incorporate a plurality of the semiconductor nanoparticles. The microbeads may possess an average diameter of around 20 nm to around 0.5 mm. The optically transparent medium may include a material such as a polymer, a resin, a monolith, a glass, a sol gel, an epoxy, a silicone, and/or a (meth)acrylate. The optically transparent medium may include a poly(methyl (meth)acrylate), poly(ethylene glycol dimethacrylate), poly(vinyl acetate), poly(divinyl benzene), poly(thioether), silica, polyepoxide, and/or combinations thereof. Alternatively, the optically transparent medium may include a copolymer of poly(methyl (meth)acrylate), poly(ethylene glycol dimethacrylate) and poly(vinyl acetate); polystyrene, polydivinyl benzene and a polythiol; and/or a copolymer of 3-(trimethoxysilyl) propylmethacrylate and tetramethoxy silane.

At least some of the nanoparticle-containing microbeads may include a core including a first optically transparent medium and one or more outer layers of the same or one or more different optically transparent media deposited on the core. The semiconductor nanoparticles may be confined to the core of the microbeads or may be dispersed throughout the core and/or one or more of the outer layers of the microbeads.

The LED encapsulation medium may include a polymer, an epoxy, a silicone, and/or a (meth)acrylate. The LED encapsulation medium may be, e.g., silica glass, silica gel, siloxane, sol gel, hydrogel, agarose, cellulose, epoxy, polyether, polyethylene, polyvinyl, poly-diacetylene, polyphenylene-vinylene, polystyrene, polypyrrole, polyimide, polyimidazole, polysulfone, polythiophene, polyphosphate, poly(meth)acrylate, polyacrylamide, polypeptide, polysaccharide, and/or combinations thereof.

The semiconductor nanoparticles may contain ions selected from group 11, 12, 13, 14, 15 and/or 16 of the periodic table, or the quantum dots may contain one or more types of transition metal ion or d-block metal ion. The semiconductor nanoparticles may contain one or more of CdS, CdSe, CdTe, ZnS, ZnSe, ZnTe, InP, InAs, InSb, AlP, AlS, AlAs, AlSb, GaN, GaP, GaAs, GaSb, PbS, PbSe, Si, Ge, MgS, MgSe, MgTe, and combinations thereof.

Some embodiments of the present invention may feature a method for preparing a formulation for use in the fabrication of a light-emitting device. The method may include incorporating a population of semiconductor nanoparticles into a plurality of discrete microbeads comprising an optically transparent medium. The nanoparticle-containing medium may be embedded into a host light-emitting diode encapsulation material.

One or more of the following features may be included. The incorporation of semiconductor nanoparticles into the optically transparent medium may include the polymerisation of one or more polymerisable monomers from which the optically transparent medium is to be formed in the presence of at least a portion of the semiconductor nanoparticles to be incorporated into the optically transparent medium. The polymerisation may be carried out by, e.g., suspension, dispersion, emulsion, living, anionic, cationic, RAFT, ATRP, bulk, ring closing metathesis, and/or ring opening metathesis. Alternatively, the polymerisation may be suspension polymerisation involving thermal curing of the one or more polymerisable monomers.

The polymerisable monomers may include methyl (meth) acrylate, ethylene glycol dimethacrylate, and vinyl acetate.

The incorporation of semiconductor nanoparticles into the optically transparent medium may include physical attachment of at least a portion of the semiconductor nanoparticles to prefabricated polymeric beads. The attachment may be achieved by, e.g., immobilisation of the portion of the semiconductor nanoparticles within the polymer matrix of the prefabricated polymeric beads, or by chemical, covalent, ionic, or physical connection between the portion of semiconductor nanoparticles and the prefabricated polymeric beads.

The prefabricated polymeric beads may include polystyrene, polydivinyl benzene, and a polythiol.

The nanoparticle-containing medium may be embedded into the host light-emitting diode encapsulation material by mixing the nanoparticle-containing medium with the encapsulation material until the nanoparticle-containing medium is substantially evenly dispersed throughout the encapsulation medium.

The semiconductor nanoparticles may be produced by converting a nanoparticle precursor composition to the material of the nanoparticles in the presence of a molecular cluster compound under conditions permitting seeding and growth of the nanoparticles on the cluster compound.

The semiconductor nanoparticles incorporate first and second ions and the nanoparticle precursor composition comprises separate first and second nanoparticle precursor species containing said first and second ions respectively for incorporation into the growing nanoparticles.

The semiconductor nanoparticles may incorporate first and second ions, and the nanoparticle precursor composition may include a single molecular species containing the first and second ions for incorporation into the growing nanoparticles.

Still other embodiments of the invention may feature a light-emitting device. The light-emitting device may include a primary light source in optical communication with a formulation including a population of semiconductor nanoparticles incorporated into a plurality of discrete microbeads comprising an optically transparent medium. The nanoparticle-containing medium may be embedded in a host light-emitting diode encapsulation medium.

The primary light source may be, e.g., a light-emitting diode, a laser, an arc lamp, and/or a black-body light source. The formulation may include a population of semiconductor nanoparticles incorporated into a plurality of discrete microbeads comprising an optically transparent medium, the nanoparticle-containing medium being embedded in a host light-emitting diode encapsulation medium.

Yet other embodiments of the invention may feature a method of fabricating a light-emitting device. The method includes providing a population of semiconductor nanoparticles in a plurality of discrete microbeads comprising an optically transparent medium. The nanoparticle-containing medium is embedded in a host light-emitting diode encapsulation material to produce a nanoparticle-containing formulation. The formulation is deposited onto a primary light source such that the primary light source is in optical communication with the population of semiconductor nanoparticles.

The encapsulation medium may be cured after being deposited onto the primary light source. The formulation may include a population of semiconductor nanoparticles incorporated into a plurality of discrete microbeads comprising an optically transparent medium, the nanoparticle-containing medium being embedded in a host light-emitting diode (LED) encapsulation medium.

BRIEF DESCRIPTION OF FIGURES

Embodiments of the present invention is illustrated with reference to the following non-limiting examples and figures in which:

FIG. 3b being a spectra for a quadchromatic-triple quantum dot light-emitting device. Note: all spectra have 1931 CIE x,y coordinates of 0.311, 0.324 and color rendering index increases from a to b;

DETAILED DESCRIPTION

A first aspect of the present invention provides a formulation for use in the fabrication of a light-emitting device, the formulation including a population of semiconductor nanoparticles incorporated into a plurality of discrete microbeads comprising an optically transparent medium, the nanoparticle-containing medium being embedded in a host light-emitting diode (LED) encapsulation medium.

Figure 1:
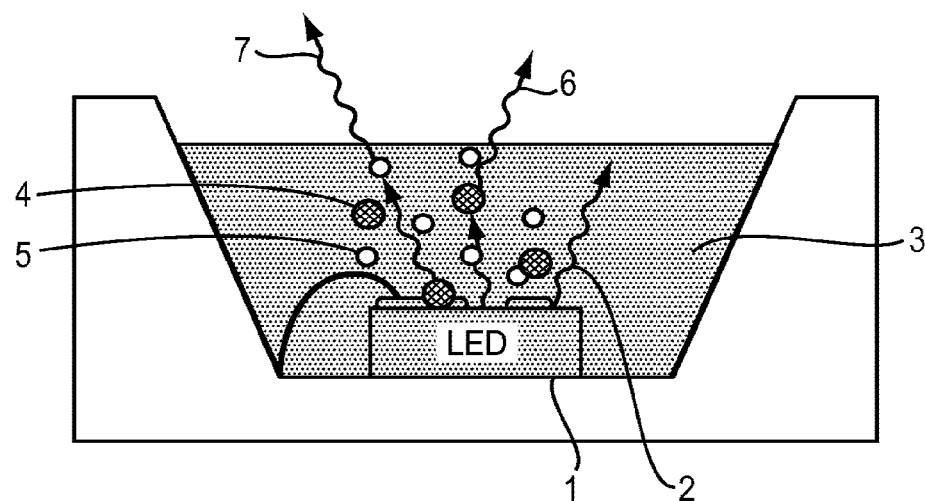
FIG. 1 is a schematic drawing depicting a quantum dot-based light-emitting device according to an aspect of the present invention.
Figure 2:
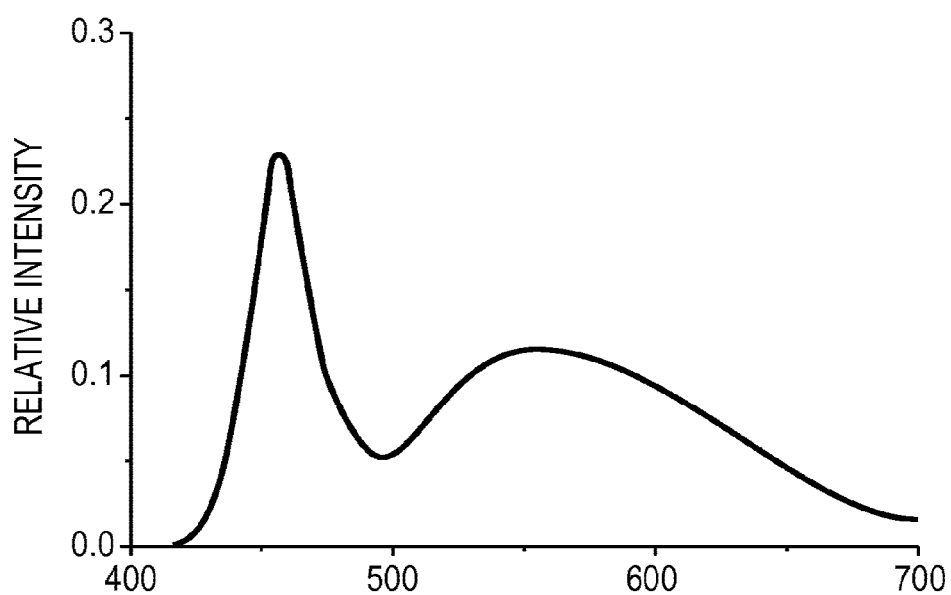
FIG. 2 is a graph illustrating white light from a conventional light-emitting device employing a blue emitting LED in combination with a broad emitting green-orange phosphor.
Figure 3A:
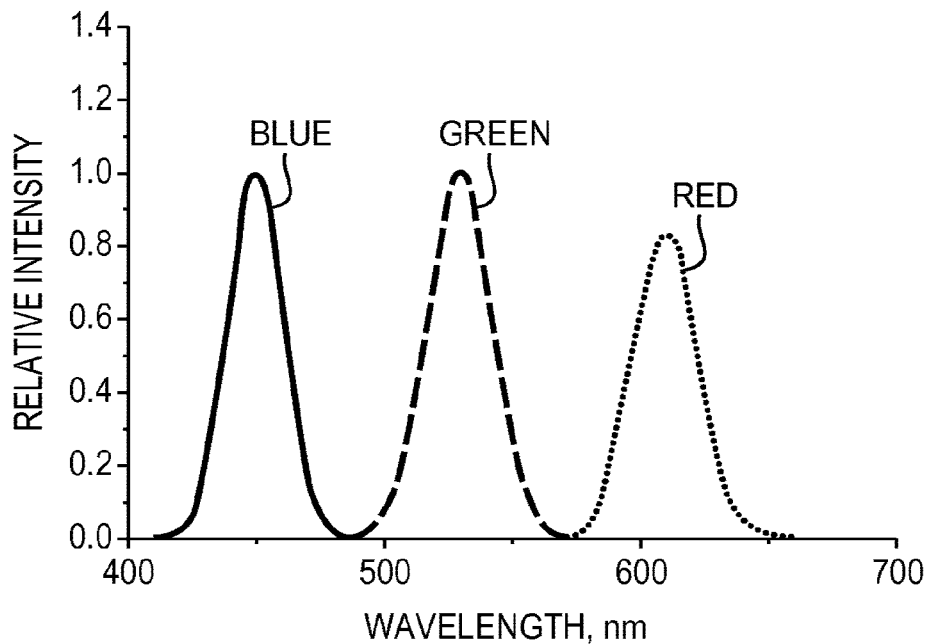
FIGS. 3a and 3b include simulated spectra relating to theoretical white light-emitting devices with FIG. 3a being a spectra for a trichromatic-dual quantum dot light-emitting device.
Figure 3B:
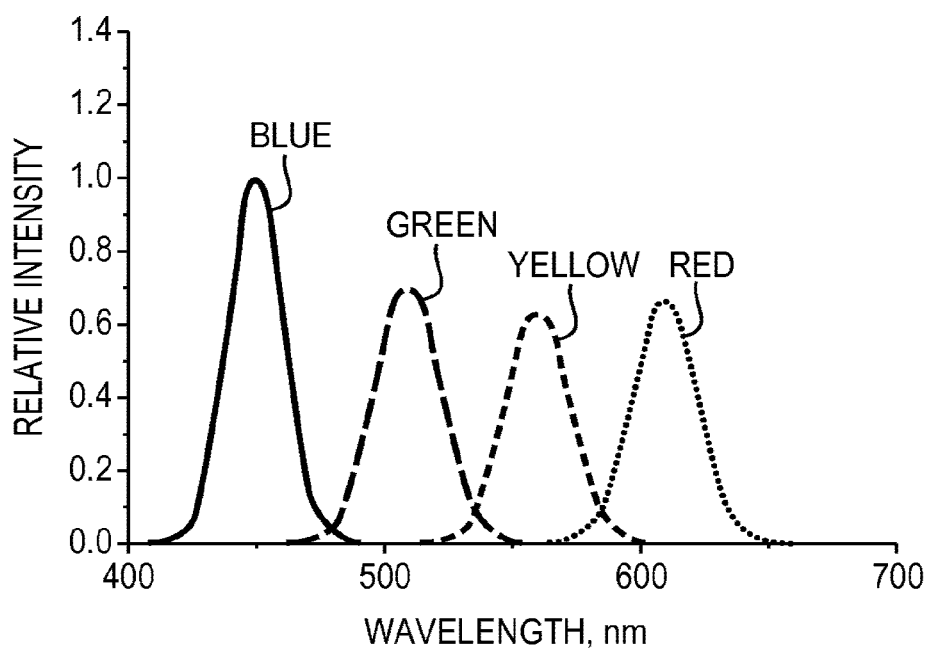

Embodiments of the current invention provide a semiconductor nanoparticle formulation for use in the fabrication of light-emitting devices, preferably with the devices incorporating an LED as a primary light source and the semiconductor nanoparticles as a secondary light source. In a preferred embodiment, the formulation contains one or more quantum dots incorporated into a plurality of polymeric beads embedded or entrapped within a host LED encapsulation material such as a silicone, an epoxy resin, a (meth)

acrylate or a polymeric material. Such an arrangement is depicted schematically in FIG. 1, where an LED 1 that is arranged to emit blue primary light 2 upon the application of current is submerged in a commercially available LED encapsulant 3 in which is embedded a plurality of quantum dot-containing polymeric beads 4, 5; a proportion of the beads 4 containing quantum dots that emit red secondary light 6 upon excitation by the blue primary light from the LED 1, and the remainder containing quantum dots 4 that emit green secondary light 7 upon excitation by the blue primary light from the LED 1.

In the Comparative Example below, an LED-based light-emitting device incorporating a formulation according to the first aspect of the present invention is tested against a light-emitting device incorporating "naked" quantum dots embedded directly in an LED encapsulant analogous to prior art methods. The device incorporating the formulation according to embodiments of the present invention was observed to perform significantly better than the prior art device in that the quantum dot-containing beads (QD-bead) were more robust in the silicone LED encapsulant used and the device exhibited an enhanced LED lifetime.

The term "beads" is used for convenience and is not intended to impose any particular size or shape limitation. Thus, for example, the beads may be spherical but other configurations are possible, such as disc- or rod-like. Where reference is made herein to "microbeads" this is intended to refer to "beads" as defined above having a dimension on the micron scale.

The nanoparticle-containing optically transparent medium is provided in the form of a plurality of discrete, i.e., separate or distinct, microbeads. For the avoidance of doubt, reference to microbeads as being "discrete" is not intended to exclude composite materials formed by aggregations of microbeads, since even in such materials each microbead retains its original bead-like structure, despite being in contact with one or more other microbeads. By pre-loading small microbeads that can range in size from 50 nm to 500 µm, or more preferably 25 nm to 0.1 mm, or more preferably still 20 nm to 0.5 mm in diameter, with quantum dots, then incorporating one or more of these quantum dot-containing beads into an LED encapsulation material on a UV or blue LED, it becomes a simple process to change, in a controllable and reproducible manner, the color of the light emitted by the LED device. Moreover, it has been shown that this approach is typically simpler than attempting to incorporate the quantum dots directly into an LED encapsulate (for example, a silicone, an epoxy, a (meth)acrylate, a polymeric material or the like) in terms of ease of color rendering, processing, and reproducibility and offers greater quantum dot stability to photo-oxidation.

This approach may lead to better processing; the quantum dot-containing beads can be made to the same size as the currently employed YAG phosphor material which range from 10 to 100 µm and can thus be supplied to commercial manufacturers in a similar form to that of the current commercially used phosphor material. Moreover, the quantum dot-containing beads are in a form that is compatible with the existing LED fabrication infrastructure.

With the advantage of very little or no loss of quantum dot quantum yield (QY) in processing, this new approach may lead to less loss of quantum efficiency than when formulating the quantum dots directly into a LED encapsulation medium. Because there is very little or no loss of quantum yield, it is easier to color render and less binning is required. It has been shown that when formulating quantum dots directly into an encapsulation medium using prior art methods, color control is very difficult due to quantum dot re-absorption or loss of quantum yield and shifting of the PL max position. Moreover batch to batch, i.e., device to device, reproducibility is very difficult or impossible to achieve. By pre-loading the quantum dots into one or more beads, the color of the light emitted by the device is easier to control and is more reproducible.

By first incorporating known amounts of quantum dots into beads before embedding the beads into the LED encapsulant, migration of moisture and oxygen is eliminated or reduced, thereby eliminating or at least reducing these hurdles to industrial production.

A second aspect of the present invention provides a method of preparing a formulation for use in the fabrication of a light-emitting device, the method including incorporating a population of semiconductor nanoparticles into a plurality of discrete microbeads comprised of an optically transparent medium, and embedding the nanoparticle-containing medium into a host light-emitting diode encapsulation material.

A third aspect of the present invention provides a light-emitting device including a primary light source in optical communication with a formulation comprising a population of semiconductor nanoparticles incorporated into a plurality of discrete microbeads comprised of an optically transparent medium, the nanoparticle-containing medium being embedded in a host light-emitting diode encapsulation medium.

A fourth aspect of the present invention provides a method of fabricating a light-emitting device, the method including providing a population of semiconductor nanoparticles in a plurality of discrete microbeads comprised of an optically transparent medium, embedding the nanoparticle-containing medium in a host light-emitting diode encapsulation material to produce a nanoparticle-containing formulation, and depositing the formulation on a primary light source such that the primary light source is in optical communication with the population of semiconductor nanoparticles.

The optically transparent medium that is to contain the semiconductor nanoparticles, preferably in the form of nanoparticle-containing beads as hereinbefore defined, may be made in the form of a resin, polymer, monolith, glass, sol gel, epoxy, silicone, (meth)acrylate or the like using any appropriate method. It is preferred that the resulting nanoparticle-containing medium is suitably compatible with the LED encapsulant to enable the nanoparticle-containing medium to be embedded within the encapsulant such that the chemical and physical structure of the resulting composite material (i.e., the LED encapsulant with nanoparticle-containing medium embedded therein) remains substantially unchanged during further processing to incorporate the composite into a light-emitting device and during operation of the resulting device over a reasonable lifetime for the device. Suitable optically transparent media include: poly(methyl(meth)acrylate) (PMMA); poly(ethylene glycol dimethacrylate) (PEGMA); poly(vinyl acetate) (PVA); poly(divinyl benzene) (PDVB); poly(thioether); silane monomers; epoxy polymers; and combinations thereof.

A particularly preferred optically transparent medium that has been shown to exhibit excellent processability and light-emitting device performance includes a copolymer of PMMA, PEGMA, and PVA, as described below in Example 1. Other preferred optically transparent media are exemplified below in Examples 2 to 5, which employ polystyrene microspheres with divinyl benzene and a thiol co-monomer; silane monomers (e.g., 3-(trimethoxysilyl)propylmethacrylate (TMOPMA) and tetramethoxysilane (TEOS)); and an epoxy polymer (e.g., Optocast™ 3553 from Electronic Materials, Inc., USA).

By incorporating quantum dots into an optically transparent, preferably clear, stable medium it is possible to protect the otherwise reactive quantum dots from the potentially damaging surrounding chemical environment. Moreover, by placing a number of quantum dots into a single bead, for example in the size range from 20 nm to 500 µm in diameter, the subsequent QD-bead tends to be more stable than the free "naked" quantum dots to the types of chemical, mechanical, thermal and photo-processing steps that are required to incorporate quantum dots in most commercial applications, such as when employing quantum dots as down converters in a "QD-solid-state-LED" light-emitting device.

It will be evident to one of skill in the art that the optically transparent medium may contain any desirable number and/or type of semiconductor nanoparticles. Thus, the medium may contain a single type of semiconductor nanoparticle, e.g., CdSe, of a specific size range, such that the composite material incorporating the nanoparticles incorporated within the medium emits monochromatic light of a pre-defined wavelength, i.e., color. The color of the emitted light may be adjusted by varying the type of semiconductor nanoparticle material used, e.g., changing the size of the nanoparticle, the nanoparticle core semiconductor material and/or adding one or more outer shells of different semiconductor materials. Moreover, color control can also be achieved by incorporating different types of semiconductor nanoparticles, for example, nanoparticles of different size and/or chemical composition within the optically transparent medium. Furthermore, the color and color intensity can be controlled by selecting an appropriate number of semiconductor nanoparticles within the optically transparent medium. Preferably the medium contains at least around 1000 semiconductor nanoparticles of one or more different types, more preferably at least around 10,000, more preferably at least around 50,000, and most preferably at least around 100,000 semiconductor nanoparticles of one or more different types.

The optically transparent medium may be provided in the form of a plurality of microbeads, some or all of which preferably contain one or more semiconductor nanoparticles capable of secondary light emission upon excitation by primary light emitted by a primary light source (e.g., an LED). It is preferred that the formulation according to the first aspect of the present invention contains a population of semiconductor nanoparticles distributed across a plurality of beads embedded within the LED encapsulant. Any desirable number of beads may be embedded, for example, the LED encapsulant may contain 1 to 10,000 beads, more preferably 1 to 5000 beads, and most preferably 5 to 1000 beads.

Some or all of the nanoparticle-containing microbeads may include a core including a first optically transparent medium and one or more outer layers or shells of the same or one or more different optically transparent media deposited on the core. Nanoparticles may be confined to the core region of the microbeads or may be dispersed throughout the core and/or one or more of the shell layers of the microbeads. An example of preparing a core/shell microbead containing a population of semiconductor nanoparticles is described below in Example 4.

It should also be appreciated that the LED encapsulant may have embedded therein one or more types of semiconductor nanoparticle-containing optically transparent medium. That is, two or more different types of optically transparent media (one or more containing the nanoparticles) may be embedded within the LED encapsulant. In this way, where the population of nanoparticles contains more than one different type of nanoparticle, the nature of the optically transparent media can be selected for optimum compatibility with both the different types of nanoparticles and the particular LED encapsulant used.

Advantages of quantum dot-containing beads over free quantum dots include greater stability to air and moisture, greater stability to photo-oxidation and greater stability to mechanical processing. Moreover, by pre-loading small microbeads, which can range in size from a few 50 nm to 500 µm, with quantum dots and then incorporating one or more of these quantum dot-containing beads into an LED encapsulation material on a UV or blue LED, a relatively simple process is provided to change, in a controllable and reproducible manner, the color of the light emitted by the LED-based light-emitting device.

In the Comparative Example presented below a light-emitting device according to an embodiment of the present invention incorporating QD-beads embedded within an LED encapsulant performs significantly better than a light-emitting device incorporating "naked" quantum dots embedded directly in an LED encapsulant analogous to prior art methods.

Semiconductor Nanoparticles

Any desirable type of semiconductor nanoparticle may be employed in the formulation of the first aspect of the present invention and the methods and devices forming the second, third and fourth aspects of the present invention. In a preferred embodiment of the formulation according to the first aspect of the present invention the nanoparticle contains ions, which may be selected from any desirable group of the periodic table, such as but not limited to group 11, 12, 13, 14, 15 or 16 of the periodic table. The nanoparticle may incorporate transition metal ions or d-block metal ions. It is preferred that the nanoparticles contain first and second ions with the first ion preferably selected from group 11, 12, 13 or 14 and the second ion preferably selected from group 14, 15 or 16 of the periodic table. The nanoparticles may contain one or more semiconductor materials such as, for example, CdS, CdSe, CdTe, ZnS, ZnSe, ZnTe, InP, InAs, InSb, AlP, AlS, AlAs, AlSb, GaN, GaP, GaAs, GaSb, PbS, PbSe, Si, Ge, MgS, MgSe, MgTe, and combinations thereof. Moreover, the nanoparticles may be binary, tertiary or quaternary core, core-shell or core-multi shell, doped or graded nanoparticles as are known to one of skill in the art.

Any appropriate method may be employed to produce the semiconductor nanoparticles employed in the various aspects of the present invention. The semiconductor nanoparticles are preferably produced by converting a nanoparticle precursor composition to the material of the nanoparticles in the presence of a molecular cluster compound under conditions permitting seeding and growth of the nanoparticles on the cluster compound. Conveniently, the nanoparticles incorporate first and second ions and the nanoparticle precursor composition comprises first and second nanoparticle precursor species containing the first and second ions respectively which are combined, preferably in the presence of a molecular cluster compound, as exemplified below in Synthetic Methods 1 and 2. The first and second precursor species may be separate species in the precursor composition or may form part of a single molecular species containing both the first and second ions. The method may employ the methodology set out in co-pending European patent application (Publication No. EP1743054A) and U.S. patent application Ser. No. 11/579,050, the disclosures of which are incorporated by reference herein in their entireties. The molecular cluster compound may contain third and fourth ions. At least one of the third and fourth ions is preferably different to the first and second ions contained in the first and second nanoparticle precursor species respectively. The third and fourth ions may be selected from any desirable group of the periodic table, such as but not limited to group 11, 12, 13, 14, 15 or 16 of the periodic table. The third and/or fourth ion may be a transition metal ion or a d-block metal ion. Preferably the third ion is selected from group 11, 12, 13 or 14 and the fourth ion is selected from group 14, 15 or 16 of the periodic table. By way of example, the molecular cluster compound may incorporate third and fourth ions from groups 12 and 16 of the periodic table respectively and the first and second ions derived from the first and second nanoparticle precursor species may be taken from groups 13 and 15 of the periodic table respectively as in Synthetic Method 2. Accordingly, the methods according to the first and second aspects of the present invention may employ methodology taken from the co-pending international patent application (Publication No. WO/2009/016354) and U.S. Pat. No. 7,588,828, the disclosures of which are incorporated by reference herein in their entireties.

It will be appreciated that during the reaction of the first and second nanoparticle precursor species, the first nanoparticle precursor species may be added in one or more portions and the second nanoparticle precursor species may be added in one or more portions. The first nanoparticle precursor species is preferably added in two or more portions. In this case, it is preferred that the temperature of a reaction mixture containing the first and second nanoparticle precursor species is increased between the addition of each portion of the first precursor species. Additionally or alternatively, the second nanoparticle precursor species may be added in two or more portions, whereupon the temperature of a reaction mixture containing the first and second nanoparticle precursor species may be increased between the addition of each portion of the second precursor species.

The coordination about the final inorganic surface atoms in any core, core-shell or core-multishell, doped or graded nanoparticle is typically incomplete, with highly reactive non-fully coordinated atoms acting as "dangling bonds" on the surface of the particle, which can lead to particle agglomeration. This problem is typically overcome by passivating (capping) the "bare" surface atoms with protecting organic groups.

In many cases, the capping agent is the solvent in which the nanoparticles have been prepared, and consists of a Lewis base compound, or a Lewis base compound diluted in an inert solvent such as a hydrocarbon. There is a lone pair of electrons on the Lewis base capping agent that are capable of a donor type coordination to the surface of the nanoparticle and include mono- or multi-dentate ligands such as phosphines (trioctylphosphine, triphenylphosphine, t-butylphosphine etc.), phosphine oxides (trioctylphosphine oxide, triphenylphosphine oxide etc.), alkyl phosphonic acids, alkyl-amines (hexadecylamine, octylamine etc.), arylamines, pyridines, long chain fatty acids and thiophenes but is, as one skilled in the art will know, not restricted to these materials.

In addition to the outermost layer of organic material or sheath material (capping agent) helping to inhibit nanoparticle-nanoparticle aggregation, this layer can also protect the nanoparticles from their surrounding electronic and chemical environments, and provide a means of chemical linkage to other inorganic, biological or organic material, whereby the functional group is pointing away from the nanoparticle surface and is available to bond/react/interact with other available molecules, such as amines, alcohols, carboxylic acids, esters, acid chloride, anhydrides, ethers, alkyl halides, amides, alkenes, alkanes, alkynes, allenes, amino acids, azides, groups etc. but is, as one skilled in the art will know, not limited to these functionalised molecules. The outermost layer (capping agent) of a quantum dot can also consist of a coordinated ligand that processes a functional group that is polymerisable and can be used to form a polymer layer around the nanoparticle. The outermost layer can also consist of organic units that are directly bonded to the outermost inorganic layer such as via a disulphide bond between the inorganic surface (e.g., ZnS) and a thiol capping molecule. These can also possess additional functional group(s), not bonded to the surface of the particle, which can be used to form a polymer around the particle, or for further reaction/interaction/chemical linkage.

An example of a material to which nanoparticle surface binding ligands may be linked is an optically transparent medium compatible with an LED encapsulant material. There are a number of approaches to incorporate semiconductor nanoparticles, such as quantum dots, into optically transparent media by pre-coating the nanoparticles with ligands that are compatible in some way with the material of the optically transparent media. By way of example, in the preferred embodiment where the nanoparticles are to be incorporated into polymeric beads, the nanoparticles can be produced so as to possess surface ligands which are polymerizable, hydrophobic or hydrophilic or by being positively or negatively charged or by being functionalised with a reactive group capable of associating with the polymer of the polymeric beads either by chemical reaction/covalent linkage/non-covalent interaction (interchelation).

It has been determined that it is possible to take quantum dots capped with polymerisable ligands or a capping agent, such as an amine or phosphine, and incorporate these quantum dots into polymer beads, which can be embedded within a host LED encapsulant and then deposited onto a solid-state LED chip to form a quantum dot-based light-emitting device. Accordingly, the second aspect of the present invention provides a method of preparing a formulation for use in the fabrication of a light-emitting device, the method including incorporating a population of semiconductor nanoparticles into an optically transparent medium and embedding the nanoparticle-containing medium into a host light-emitting diode encapsulation material.

Incorporating Quantum Dots into Beads

Figure 6:
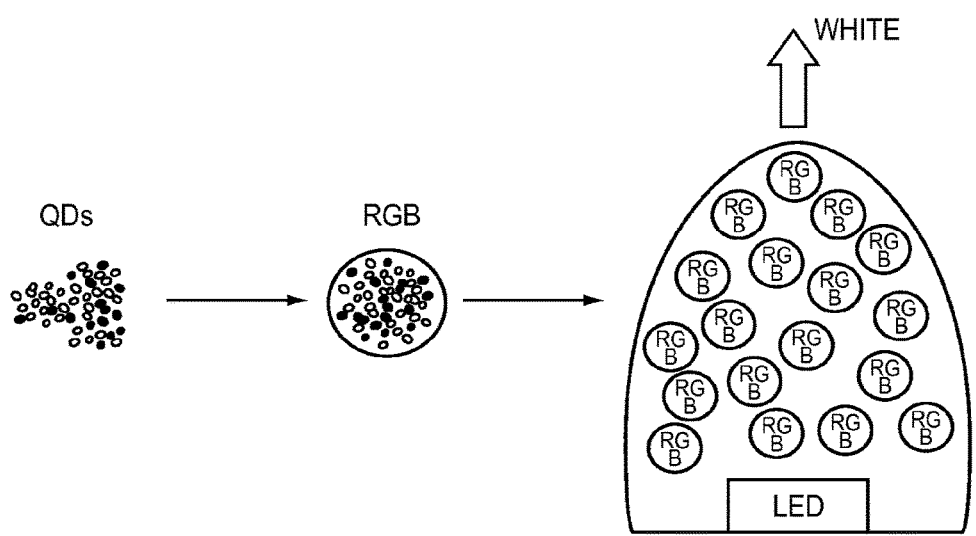
FIG. 6 is a schematic representation of a QD-bead-based light-emitting device according to an aspect of the present invention employing multi-colored, multiple quantum dot types in each bead such that each bead emits white secondary light.
Figure 7:
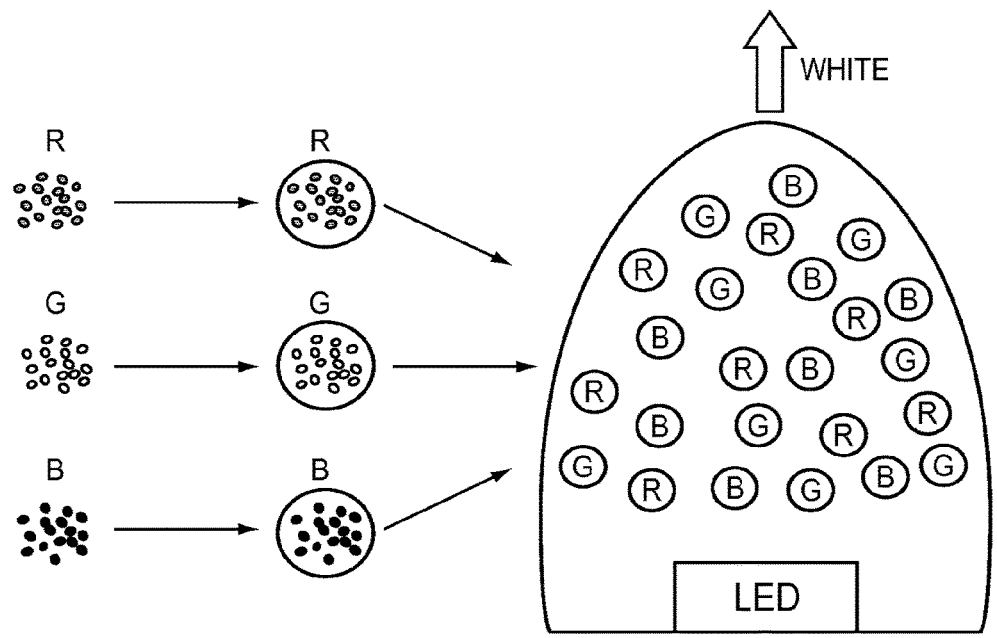
FIG. 7 is a schematic representation of a QD-bead-based light-emitting device according to an aspect of the present invention employing multi-colored, multiple quantum dot types in different beads such that each bead contains a single quantum dot type emitting a single color, a mixture of the beads combining to produce white secondary light.
Figure 8:
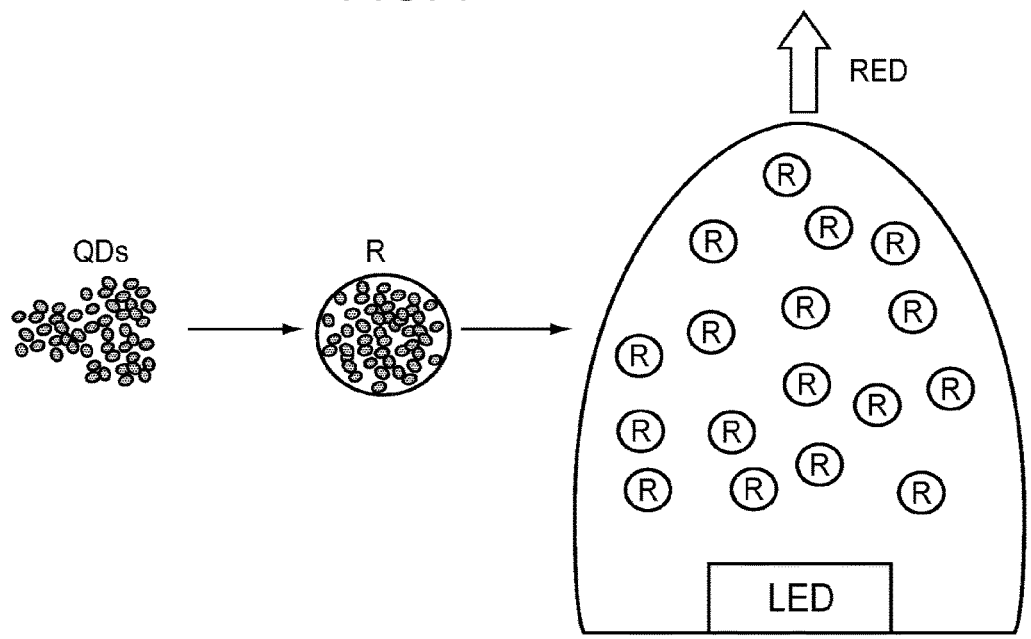
FIG. 8 is a schematic representation of a QD-bead-based light-emitting device according to an aspect of the present invention employing singly colored, single quantum dot type in all beads such that a mixture of the beads emits a single color of secondary light (in this case, red light)

Considering the initial step of incorporating quantum dots into beads, a first option is to incorporate the quantum dots directly into the polymer matrices of resin beads. A second option is to immobilise the quantum dots in polymer beads through physical entrapment. It is possible to use these methods to make a population of beads that contain just a single type of quantum dot (e.g., one color) by incorporating a single type of quantum dot into the beads. Alternatively, it is possible to construct beads that contain 2 or more types of quantum dots (e.g., two or more colors) by incorporating a mixture of two or more types of quantum dot (e.g., material and/or size) into the beads. Such mixed beads can then be combined in any suitable ratio to emit any desirable color of secondary light following excitation by the primary light emitted by the primary light source (e.g., LED). This is exemplified in FIGS. 6 to 8 that schematically show QD-bead light-emitting devices including respectively: a) multi-colored, multiple quantum dot types in each bead such that each bead emits white secondary light; b) multi-colored, multiple quantum dot types in different beads such that each bead contains a single quantum dot type emitting a single color, a mixture of the beads combining to produce white secondary light; and c) singly colored, single quantum dot type in all beads such that a mixture of the beads emits a single color of secondary light, e.g., red.

Incorporating Quantum Dots Beads During Bead Formation

With regard to the first option, by way of example, hexadecylamine-capped CdSe-based semiconductor nanoparticles can be treated with at least one, more preferably two or more polymerisable ligands (optionally one ligand in excess) resulting in the displacement of at least some of the hexadecylamine capping layer with the polymerisable ligand(s). The displacement of the capping layer with the polymerisable ligand(s) can be accomplished by selecting a polymerisable ligand or ligands with structures similar to that of trioctylphosphine oxide (TOPO), which is a ligand with a known and very high affinity for CdSe-based nanoparticles. It will be appreciated that this basic methodology may be applied to other nanoparticle/ligand pairs to achieve a similar effect. That is, for any particular type of nanoparticle (material and/or size), it is possible to select one or more appropriate polymerisable surface binding ligands by choosing polymerisable ligands comprising a structural motif which is analogous in some way (e.g., has a similar physical and/or chemical structure) to the structure of a known surface binding ligand. Once the nanoparticles have been surface-modified in this way, they can then be added to a monomer component of a number of microscale polymerisation reactions to form a variety of quantum dot-containing resins and beads. A preferred embodiment of the second aspect of the present invention comprises the polymerisation of one or more polymerisable monomers from which the optically transparent medium is to be formed in the presence of at least a portion of the semiconductor nanoparticles to be incorporated into the optically transparent medium. The resulting materials incorporate the quantum dots covalently and appear highly colored even after prolonged periods of Soxhlet extraction.

Examples of polymerisation methods that may be used to construct quantum dot-containing beads include, e.g., suspension, dispersion, emulsion, living, anionic, cationic, RAFT, ATRP, bulk, ring closing metathesis and ring opening metathesis. Initiation of the polymerisation reaction may be caused by any suitable method which causes the monomers to react with one another, such as by the use of free radicals, light, ultrasound, cations, anions, or heat. A preferred method is suspension polymerisation involving thermal curing of one or more polymerisable monomers from which the optically transparent medium is to be formed. The polymerisable monomers preferably include methyl(meth)acrylate, ethylene glycol dimethacrylate and vinyl acetate. This combination of monomers has been shown to exhibit excellent compatibility with existing commercially available LED encapsulants and has been used to fabricate a light-emitting device exhibiting significantly improved performance compared to a device prepared using essentially prior art methodology. Other preferred polymerisable monomers are epoxy or polyepoxide monomers, which may be polymerised using any appropriate mechanism, such as curing with ultraviolet irradiation.

Quantum dot-containing microbeads can be produced by dispersing a known population of quantum dots within a polymer matrix, curing the polymer and then grinding the resulting cured material. This is particularly suitable for use with polymers that become relatively hard and brittle after curing, such as many common epoxy or polyepoxide polymers (e.g., Optocast™ 3553 from Electronic Materials, Inc., USA).

Quantum dot-containing beads may be generated simply by adding quantum dots to the mixture of reagents used to construct the beads. In some instances quantum dots (nascent quantum dots) may be used as isolated from the reaction employed to synthesise them and are thus generally coated with an inert outer organic ligand layer. In an alternative procedure a ligand exchange process may be carried out prior to the bead forming reaction. Here one or more chemically reactive ligands (for example this might be a ligand for the quantum dots that also contains a polymerisable moiety) is added in excess to a solution of nascent quantum dots coated in an inert outer organic layer. After an appropriate incubation time, the quantum dots are isolated, for example by precipitation and subsequent centrifugation, washed and then incorporated into the mixture of reagents used in the bead forming reaction/process.

Both quantum dot incorporation strategies will result in statistically random incorporation of the quantum dots into the beads and thus the polymerisation reaction may result in beads containing statistically similar amounts of the quantum dots. It will be obvious to one of skill in the art that bead size can be controlled by the choice of polymerisation reaction used to construct the beads and additionally once a polymerisation method has been selected bead size can also be controlled by selecting appropriate reaction conditions, e.g., in a suspension polymerisation reaction by stirring the reaction mixture more quickly to generate smaller beads. Moreover the shape of the beads can be readily controlled by choice of procedure in conjunction with whether or not the reaction is carried out in a mould. The composition of the beads can be altered by changing the composition of the monomer mixture from which the beads are constructed. Similarly the beads can also be cross-linked with varying amounts of one or more cross-linking agents (e.g., divinyl benzene). If beads are constructed with a high degree of cross-linking, e.g., greater than 5 mol % cross-linker, it may be desirable to incorporate a porogen (e.g., toluene or cyclohexane) during the reaction used to construct the beads. The use of a porogen in such a way leaves permanent pores within the matrix constituting each bead. These pores may be sufficiently large to allow the ingress of quantum dots into the bead.

Quantum dots can also be incorporated in beads using reverse emulsion based techniques, as exemplified below in Examples 3 and 4. The quantum dots may be mixed with precursor(s) to the optically transparent coating material and then introduced into a stable reverse emulsion containing, for example, an organic solvent and a suitable salt. Following agitation, the precursors form microbeads encompassing the quantum dots, which can then be collected using any appropriate method, such as centrifugation. If desired, one or more additional surface layers or shells of the same or the different optically transparent material can be added prior to isolation of the quantum dot-containing beads by addition of further quantities of the requisite shell layer precursor material(s) as exemplified in Example 4.

Incorporating Quantum Dots into Prefabricated Beads

With respect to the second option for incorporating quantum dots into beads, the quantum dots can be immobilised in polymer beads through physical entrapment. For example, a solution of quantum dots in a suitable solvent (e.g., an organic solvent) can be incubated with a sample of polymer beads. Removal of the solvent using any appropriate method results in the quantum dots becoming immobilised within the matrix of the polymer beads. The quantum dots remain immobilised in the beads unless the sample is resuspended in a solvent (e.g., organic solvent) in which the quantum dots are freely soluble. Optionally, at this stage the outside of the beads can be sealed. A further preferred embodiment of the second aspect of the present invention comprises the physical attachment of at least a portion of the semiconductor nanoparticles to prefabricated polymeric beads. The attachment may be achieved by immobilisation of the portion of the semiconductor nanoparticles within the polymer matrix of the prefabricated polymeric beads or by chemical, covalent, ionic, or physical connection between the portion of semiconductor nanoparticles and the prefabricated polymeric beads. In a particularly preferred embodiment the prefabricated polymeric beads comprise polystyrene, polydivinyl benzene and a polythiol.

Quantum dots may be irreversibly incorporated into prefabricated beads in a number of ways, e.g., chemical, covalent, ionic, physical (e.g., by entrapment) or any other form of interaction. If prefabricated beads are to be used for the incorporation of quantum dots, the solvent accessible surfaces of the bead may be chemically inert (e.g., polystyrene) or alternatively they may be chemically reactive/functionalised (e.g., Merrifield's Resin). The chemical functionality may be introduced during the construction of the bead, for example by the incorporation of a chemically functionalised monomer, or alternatively chemical functionality may be introduced in a post bead construction treatment, for example by conducting a chloromethylation reaction. Additionally, chemical functionality may be introduced by a post bead construction polymeric graft or other similar process whereby chemically reactive polymer(s) are attached to the outer layers/accessible surfaces of the bead. It will be obvious to one of skill in the art that more than one such post construction derivatisation process may be carried out to introduce chemical functionality onto/into the bead.

As with quantum dot incorporation into beads during the bead forming reaction, i.e., the first option described above, the pre-fabricated beads can be of any shape, size and composition and may have any degree of cross-linker and may contain permanent pores if constructed in the presence of a porogen. Quantum dots may be imbibed into the beads by incubating a solution of quantum dots in an organic solvent and adding this solvent to the beads. The solvent must be capable of wetting the beads and in the case of lightly cross-linked beads, preferably 0-10% cross-linked and most preferably 0-2% cross-linked the solvent should cause the polymer matrix to swell in addition to solvating the quantum dots. Once the quantum dot-containing solvent has been incubated with the beads, it is removed, for example by heating the mixture and causing the solvent to evaporate and the quantum dots to become embedded in the polymer matrix constituting the bead or alternatively by the addition of a second solvent in which the quantum dots are not readily soluble but which mixes with the first solvent causing the quantum dots to precipitate within the polymer matrix constituting the beads. Immobilisation may be reversible if the bead is not chemically reactive or else if the bead is chemically reactive the quantum dots may be held permanently within the polymer matrix, by chemical, covalent, ionic, or any other form of interaction.

Incorporation of Quantum Dots into Sol-Gels to Produce Glass

Optically transparent media that are sol-gels and glasses that are intended to incorporate quantum dots may be formed in an analogous fashion to the method used to incorporate quantum dots into beads during the bead forming process as described above. For example, a single type of quantum dot (e.g., one color) may be added to the reaction mixture used to produce the sol-gel or glass. Alternatively, two or more types of quantum dot (e.g., two or more colors) may be added to the reaction mixture used to produce the sol-gel or glass. The sol-gels and glasses produced by these procedures may have any shape, morphology or 3-dimensional structure. For example, the particles may be spherical, disc-like, rod-like, ovoid, cubic, rectangular or any of many other possible configurations.

Incorporating Quantum Dot-Beads into LED Encapsulant

It is a significant advantage of the present invention that quantum dot-beads (QD-beads) produced as described above can be incorporated into commercially available LED encapsulant materials simply by weighing the desired amount of QD-bead material and adding this to the desired amount of LED encapsulant material. Preferably the resulting composite is mixed thoroughly to provide a homogeneous mixture. Thus, in a preferred embodiment of the second aspect of the present invention, the nanoparticle-containing medium is embedded into the host light-emitting diode encapsulation material by mixing the nanoparticle-containing medium with the encapsulation material until the nanoparticle-containing medium is substantially evenly dispersed throughout the encapsulation medium. The QD-bead-LED-encapsulant composite may then be dispensed onto a commercially available LED and cured according to the normal curing procedure for the particular LED-encapsulant used. The QD-bead-LED encapsulant formulation according to the first aspect of the present invention thus provides a simple and straightforward way of facilitating the fabrication of next generation, higher performance light-emitting devices using, as far as possible, standard commercially available materials and methods.

LED Encapsulating Materials

Any existing commercially available LED encapsulant may be used in connection with the various aspects of the present invention. Preferred LED encapsulants include silicones, epoxies, (meth)acrylates and other polymers, although it will be appreciated by one of skill in the art that further options are available, such as but not limited to silica glass, silica gel, siloxane, sol gel, hydrogel, agarose, cellulose, epoxy, polyether, polyethylene, polyvinyl, poly-di-acetylene, polyphenylene-vinylene, polystyrene, polypyrrole, polyimide, polyimidazole, polysulfone, polythiophene, polyphosphate, poly(meth)acrylate, polyacrylamide, polypeptide, polysaccharide, and combinations thereof.

LED encapsulants that may be used in the various aspects of the present invention include, but are not limited to, UV curable encapsulants and heat curable encapsulants, including encapsulants that require one or more catalysts to support the curing process. Specific examples of commercially available silicone encapsulants that are suitable for use with aspects of the present invention may be, for example, SCR1011, SCR1012, SCR1016, and/or LPS-3412 (all available from Shin Etsu) and examples of suitable epoxy encapsulants may be, for example, Pacific Polytech PT1002, Fine Polymers Epifine EX-1035A, and/or Fine Polymers Epifine X-1987.

Color Indexing

The color of the light output from the QD-bead-LED (the "secondary light") can be measured using a spectrometer. The spectral output (mW/nm) can then be processed mathematically so that the particular color of the light-emitting device can be expressed as color coordinates on a chromaticity diagram, for example the 2° CIE 1931 chromaticity diagram (see FIG. 4).

Figure 5:
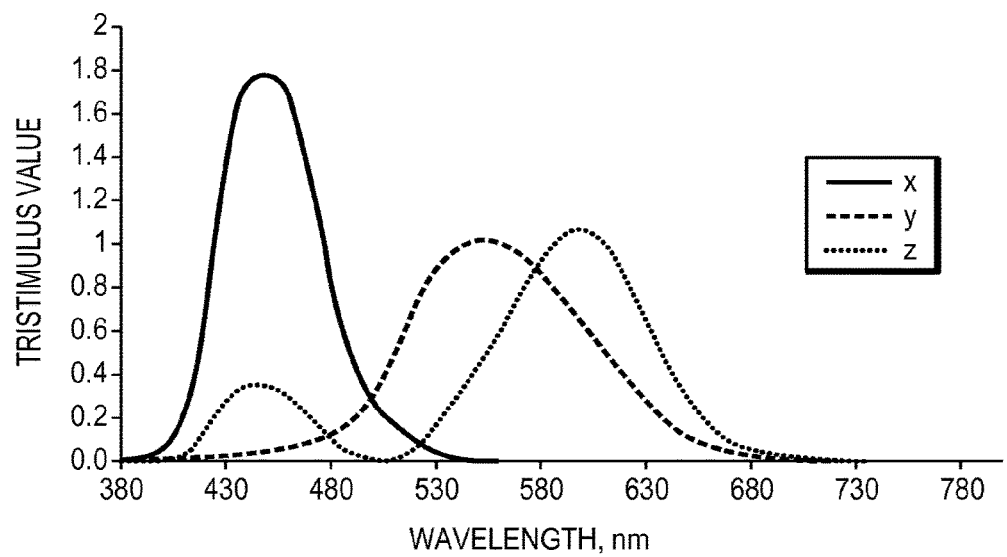
FIG. 5 is a 2° CIE 1931 color matching diagram matching functions x, y, z.

The 2° CIE 1931 chromaticity coordinates for a particular spectrum can be calculated from the spectral power distribution and the CIE 1931 color matching functions x, y, z (see FIG. 5). The corresponding tristimulus values can be calculated thus $$X = \int p x\, d\lambda, Y = \int p y\, d\lambda, Z = \int p z\, d\lambda.$$

Where p is the spectral power, and x, y and z are the color matching functions.

From X, Y, and Z the chromaticity coordinates x, y can be calculated according to $$x = \frac{X}{X+Y+Z} \text{ and } y = \frac{Y}{X+Y+Z}$$

Figure 4:
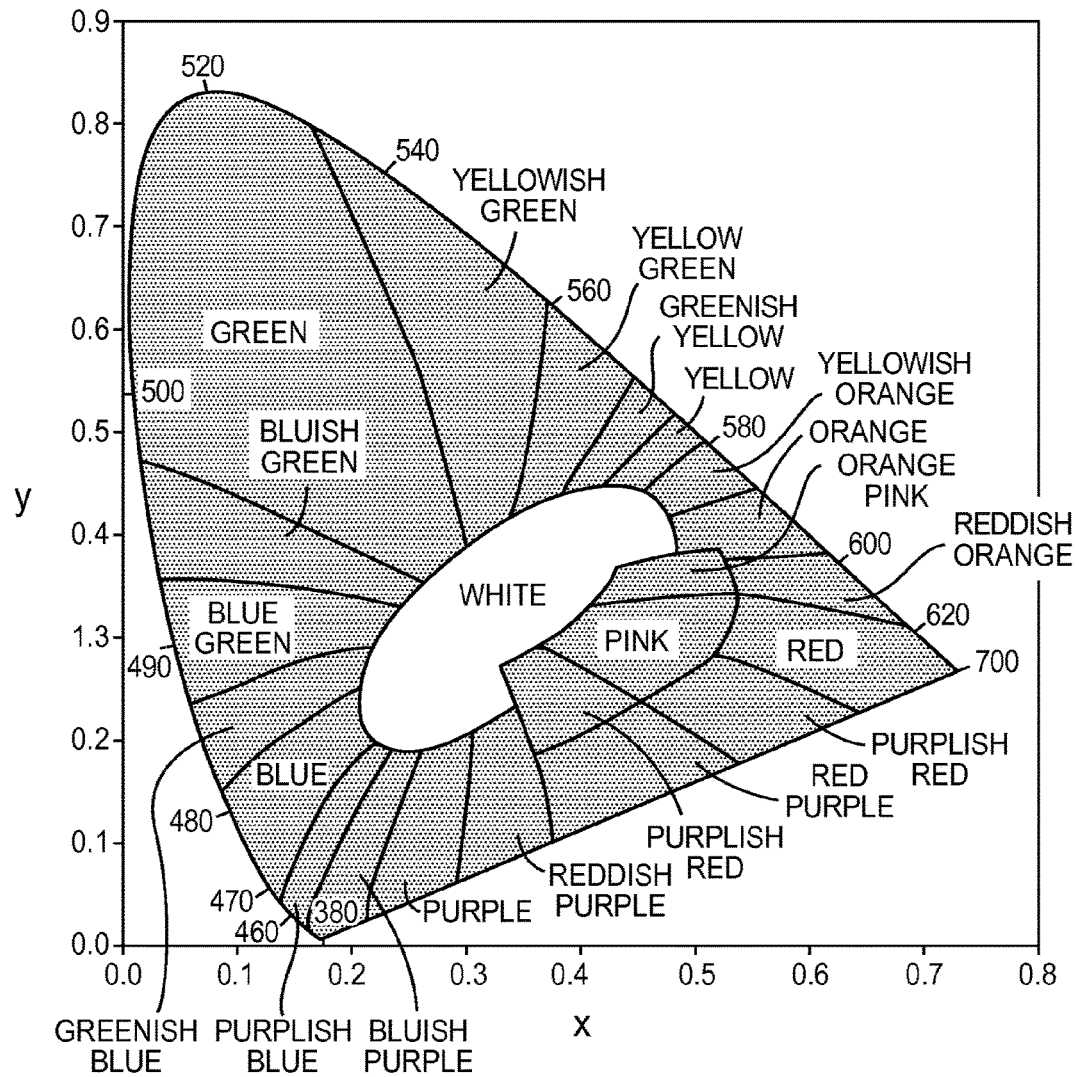
FIG. 4 is a 2° CIE 1931 chromaticity diagram.

Using x, y as the coordinates, a two-dimensional chromaticity diagram (the CIE 1931 color space diagram) can be plotted which is analogous to the exemplary diagram depicted in FIG. 4.

Color Rendering

Color rendering describes the ability of a light source to illuminate objects such that they appear the correct color when compared to how they appear when illuminated by a reference light source. Usually the reference light source is a tungsten filament bulb which is assigned a color rendering index (CRI) of 100. To be acceptable for general lighting, a white light-emitting device source is required to have a CRI>80. An example of poor color rendering is the sodium street lamp that has very poor color rendering capability, i.e., it is difficult to distinguish a red car from a yellow car illuminated by a sodium lamp; in the dark under a sodium lamp they both appear grey.

Embodiments of the present invention provide a light-emitting device comprising a population of quantum dots incorporated into an optically transparent medium (e.g., polymeric beads) which are embedded within a host light-emitting diode (LED) encapsulation material/medium (e.g., epoxy resin, silicone, acrylate, etc). The quantum dots within the optically transparent medium are in optical communication with a primary solid-state photon/light source (e.g., an LED, laser, arc lamp or black-body light source) such that, upon excitation by primary light from the primary light source, the quantum dots within the optically transparent medium emit secondary light of a desired color. The required intensities and emission wavelengths of the light emitted from the device itself can be selected according to appropriate mixing of the color of the primary light with that of the secondary light(s) produced from the down conversion of the primary light by the quantum dots. Moreover, the size (and thus emission) and number of each type of quantum dot within the optically transparent medium can be controlled, as can the size, morphology and constituency of the optically transparent medium, such that subsequent mixing of the quantum dot-containing media allows light of any particular color and intensity to be produced.

It will be appreciated that the overall light emitted from the device may consist of effectively just the light emitted from the quantum dots, i.e., just the secondary light, or a mixture of light emitted from the quantum dots and light emitted from the solid-state/primary light source, i.e., a mixture of the primary and secondary light. Color mixing of the quantum dots can be achieved either within the quantum dot-containing media (e.g., within each bead in a population of beads such that each bead contains a number of different size/color emitting quantum dots) or a mixture of differently colored optically transparent media (e.g., beads) with all the quantum dots within a specific medium being the same size/color (e.g., some beads containing all green quantum dots and others containing all red quantum dots).

EXAMPLES

Examples 1 to 5 below describe the preparation of quantum dot-containing formulations for use in the fabrication of new, improved quantum dot-based light-emitting devices in accordance with embodiments of the present invention. In the Comparative Example, a device in accordance with an embodiment of the present invention is tested against a device based on prior art principles using the same type of quantum dots to compare the performance of the two devices. Two methods for producing quantum dots suitable for incorporation into the formulations are first set out in the Synthetic Methods section below.

Synthetic Methods

Method 1

CdSe/ZnS hexadecylamine-capped quantum dots were prepared as described below for subsequent processing into a quantum-dot-containing formulation for use in the fabrication of a light-emitting device in accordance with embodiments of the present invention.

Preparation of CdSe-HDA Capped Core Quantum Dots

HDA (500 g) was placed in a three-neck round bottomed flask and dried and degassed by heating to 120° C. under a dynamic vacuum for >1 hour. The solution was then cooled to 60° C. To this was added 0.718 g of $[HNEt_3]_4[Cd_{10}Se_4(SPh)_{16}]$ (0.20 mmols). In total 42 mmols, 22.0 ml of TOPSe and 42 mmols, (19.5 ml, 2.15 M) of $Me_2Cd.TOP$ was used. Initially 4 mmol of TOPSe and 4 mmols of $Me_2Cd.TOP$ were added to the reaction at room temperature and the temperature increased to 110° C. and allowed to stir for 2 hours. The reaction was a deep yellow color. The temperature was progressively increased at a rate of ~1° C./5 min with equimolar amounts of TOPSe and $Me_2Cd.TOP$ being added dropwise. The reaction was stopped when the PL emission maximum had reached ~600 nm, by cooling to 60° C. followed by addition of 300 ml of dry ethanol or acetone. This produced a precipitation of deep red particles, which were further isolated by filtration. The resulting CdSe particles were recrystallized by re-dissolving in toluene followed by filtering through Celite followed by re-precipitation from warm ethanol to remove any excess HDA, selenium or cadmium present. This produced 10.10 g of HDA capped CdSe nanoparticles. Elemental analysis C=20.88, H=3.58, N=1.29, Cd=46.43%. Max PL=585 nm, FWHM=35 nm. 38.98 mmols, 93% of $Me_2Cd$ consumed in forming the quantum dots.

Growth of ZnS Shell to Provide CdSe/ZnS-HDA Capped Core/Shell Quantum Dots

HDA (800 g) was placed in a three-neck round-bottom flask, and dried and degassed by heating to 120° C. under a dynamic vacuum for >1 hour. The solution was then cooled to 60° C.; to this was added 9.23 g of CdSe nanoparticles that have a PL maximum emission of 585 nm. The HDA was then heated to 220° C. To this was added by alternate dropwise addition a total of 20 ml of 0.5 M $Me_2Zn.TOP$ and 0.5 M, 20 ml of sulfur dissolved in octylamine. Three alternate additions of 3.5, 5.5 and 11.0 ml of each were made, whereby initially 3.5 ml of sulphur was added dropwise until the intensity of the PL maximum was near zero. Then 3.5 ml of $Me_2Zn.TOP$ was added dropwise until the intensity of the PL maximum had reached a maximum. This cycle was repeated with the PL maximum reaching a higher intensity with each cycle. On the last cycle, additional precursor was added once the PL maximum intensity been reached until it was between 5-10% below the maximum intensity, and the reaction was allowed to anneal at 150° C. for 1 hour. The reaction mixture was then allowed to cool to 60° C. whereupon 300 ml of dry "warm" ethanol was added, which resulted in the precipitation of particles. The resulting CdSe—ZnS particles were dried before re-dissolving in toluene and filtering through Celite followed by re-precipitation from warm ethanol to remove any excess HDA. This produced 12.08 g of HDA capped CdSe—ZnS core-shell nanoparticles. Elemental analysis C=20.27, H=3.37, N=1.25, Cd=40.11, Zn=4.43%; Max PL 590 nm, FWHM 36 nm.

Method 2

InP quantum dots were prepared as described below which can then be processed into a quantum-dot-containing formulation for use in the fabrication of a light-emitting device in accordance with embodiments of the present invention.

Preparation of InP Core Quantum Dots (500-700 nm Emission)

Di-butyl ester (100 ml) and Myristic acid (10.0627 g) were placed in a three-neck flask and degassed at 70° C. under vacuum for one hour. After this period, nitrogen was introduced and the temperature increased to 90° C. ZnS molecular cluster $[Et_3NH_4][Zn_{10}S_4(SPh)_{16}]$ (4.7076 g) was added and the mixture allowed to stir for 45 minutes. The temperature was then increased to 100° C. followed by the dropwise addition of $In(MA)_3$ (1 M, 15 ml) followed by $(TMS)_3P$ (1 M, 15 ml). The reaction mixture was allowed to stir while increasing the temperature to 140° C. At 140° C., further dropwise additions of $In(MA)_3$ (1 M, 35 ml) (left to stir for 5 minutes) and $(TMS)_3P$ (1 M, 35 ml) were made. The temperature was then slowly increased to 180° C. and further dropwise additions of $In(MA)_3$ (1 M, 55 ml) followed by $(TMS)_3P$ (1 M, 40 ml) were made. By addition of the precursor in the above manner, nanoparticles of InP could be grown with the emission maximum gradually increasing from 520 nm up to 700 nm, whereby the reaction can be stopped when the desired emission maximum has been obtained and left to stir at this temperature for half an hour. After this period, the temperature was decreased to 160° C. and the reaction mixture was left to anneal for up to 4 days (at a temperature between 20-40° C. below that of the reaction). A UV lamp was also used at this stage to aid in annealing.

The nanoparticles were isolated by the addition of dried degassed methanol (approx. 200 ml) via cannula techniques. The precipitate was allowed to settle and then methanol was removed via cannula with the aid of a filter stick. Dried degassed chloroform (approx. 10 ml) was added to wash the solid. The solid was left to dry under vacuum for 1 day. This produced 5.60 g of InP core nanoparticles. Elemental analysis: max PL=630 nm, FWHM=70 nm.

Post-Operative Treatments

The quantum yields of the InP quantum dots prepared above were increased by washing with dilute HF acid. The dots were dissolved in anhydrous degassed chloroform (~270 ml). A 50 ml portion was removed and placed in a plastic flask, flushed with nitrogen. Using a plastic syringe, the HF solution was made up by adding 3 ml of 60% w/w HF in water and adding to degassed THF (17 ml). The HF was added dropwise over 5 hrs to the InP dots. After addition was complete the solution was left to stir overnight. Excess HF was removed by extracting through calcium chloride solution in water and drying the etched InP dots. The dried dots were re-dispersed in 50 ml chloroform for future use. Max 567 nm, FWHM 60 nm. The quantum efficiencies of the core materials at this stage range from 25-90%.

Growth of a ZnS Shell to Provide InP/ZnS Core/Shell Quantum Dots

A 20 ml portion of the HF etched InP core particles was dried down in a 3-neck flask 1.3 g myristic acid and 20 ml di-n-butyl sebacate ester was added and degassed for 30 minutes. The solution was heated to 200° C. then 1.2 g anhydrous zinc acetate was added and 2 ml 1 M $(TMS)_2S$ was added dropwise (at a rate of 7.93 ml/hr) after addition was complete the solution was left to stir. The solution was kept at 200° C. for 1 hr then cooled to room temperature. The particles were isolated by adding 40 ml of anhydrous degassed methanol and centrifuged. The supernatant liquid was disposed of, and 30 ml of anhydrous degassed hexane was added to the remaining solid. The solution was allowed to settle for 5 hrs and then re-centrifuged. The supernatant liquid was collected and the remaining solid was discarded. PL emission peak Max.=535 nm, FWHM=65 nm. The quantum efficiencies of the nanoparticle core/shell materials at this stage ranged from 35-90%.

Example 1

Incorporation of Quantum Dots into Suspension Polymeric Beads

1% wt/vol polyvinyl acetate (PVA) (aq) solution was prepared by stirring for 12 hours followed by extensive degassing by bubbling nitrogen through the solution for a minimum of 1 hour. The monomers, methyl methacrylate and ethylene glycol dimethacrylate, were also degassed by nitrogen bubbling and used with no further purification. The initiator AIBN (0.012 g) was placed into the reaction vessel and put under three vacuum/nitrogen cycles to ensure no oxygen was present.

CdSe/ZnS core/shell quantum dots as prepared above in Method 1 were added to the reaction vessel as a solution in toluene and the solvent removed under reduced pressure. Degassed methyl methacrylate (0.98 mL) was then added followed by degassed ethylene glycol dimethacrylate (0.15 mL). The mixture was then stirred at 800 rpm for 15 minutes to ensure complete dispersion of the quantum dots within the monomer mixture. The solution of 1% PVA (10 mL) was then added and the reaction stirred for 10 minutes to ensure the formation of the suspension. The temperature was then raised to 72° C. and the reaction allowed to proceed for 12 hours.

The reaction mixture was then cooled to room temperature and the beaded product washed with water until the washings ran clear followed by methanol (100 mL), methanol/tetrahydrofuran (1:1, 100 mL), tetrahydrofuran (100 mL), tetrahydrofuran/dichloromethane (1:1, 100 mL), dichloromethane (100 mL), dichloromethane/tetrahydrofuran (1:1, 100 mL), tetrahydrofuran (100 mL), tetrahydrofuran/methanol (1:1, 100 mL), methanol (100 mL). The quantum dot-containing beads (QD-beads) were then dried under vacuum and stored under nitrogen.

The quantum dot-containing resin suspension beads prepared above were transferred into vials under an inert atmosphere. An LED encapsulant (Shin Etsu SCR1011 or Shin Etsu SCR1016) was then added and the mixture stirred to ensure good dispersion within the encapsulating polymer. The encapsulant mixture was then transferred to a well in an LED chip and cured under an inert atmosphere using standard conditions for the LED encapsulant used.

Example 2

Adsorbing of Quantum Dots into Prefabricated Beads

Polystyrene microspheres with 1% divinyl benzene (DVB) and 1% thiol co-monomer were resuspended in toluene (1 mL) by shaking and sonication. The microspheres were centrifuged (6000 rpm, approx 1 min) and the supernatant decanted. This was repeated for a second wash with toluene and the pellets then resuspended in toluene (1 mL).

InP/ZnS quantum dots as prepared above in Method 2 were dissolved (an excess, usually 5 mg for 50 mg of microspheres) in chloroform (0.5 mL) and filtered to remove any insoluble material. The quantum dot-chloroform solution was added to the microspheres in toluene and shaken on a shaker plate at room temperature for 16 hours to mix thoroughly.

The quantum dot-microspheres were centrifuged to pellet and the supernatant decanted off, which contained any excess quantum dots present. The pellet was washed (as above) twice with toluene (2 mL), resuspended in toluene (2 mL), and then transferred directly to glass sample vials used in an integrating sphere. The glass vials were pelleted down by placing the vials inside a centrifuge tube, centrifuging and decanting off excess toluene. This was repeated until all of the material had been transferred into the sample vial. A quantum yield analysis was then run directly on the pellet, wet with toluene.

Quantum Dot-Bead Light-Emitting Device Fabrication

The quantum dot-containing resin microspheres prepared above were transferred into vials under an inert atmosphere. An LED encapsulant (Shin Etsu SCR1011 or Shin Etsu SCR1016) was then added and the mixture stirred to ensure good dispersion within the encapsulating polymer. The encapsulant mixture was then transferred to a well in an LED chip and cured under an inert atmosphere using standard conditions for the LED encapsulant used.

Example 3

Reverse Emulsion Synthesis of Silica Beads Embedded with Quantum Dots

A solution of InP/ZnS core/steel quantum dots (containing 70 mg of inorganic material) was subjected to evaporation to remove most of the quantum dot solvent, which in this case was toluene, and then mixed with silane monomers (e.g., 0.1 mL of 3-(trimethoxysilyl)propylmethacrylate (TMOPMA) and 0.5 mL of tetramethoxy silane (TEOS)) until a clear solution was obtained.

10 mL of degassed cyclohexane/Igepal™ CO-520 (CO-520 is $C_9H_{19}$-Ph-$(OCH_2CH_2)_a$—OH where n 5) (18 mL/1.35 g) was prepared in a 50 mL flask and 0.1 mL of 4% $NH_4OH$ injected to form a stable reverse emulsion.

The quantum dot/silane mixture was then injected into the cyclohexane/CO-520/$NH_4OH$ mixture. The resulting mixture was stirred at 500 rpm under $N_2$ overnight. Silica beads containing the QDs were collected by centrifugation and washed with cyclohexane twice. The resulting sediment was then dried under vacuum.

Quantum Dot-Bead LED Fabrication

Quantum dot-containing silica microbeads prepared as described above can be mixed with an LED encapsulant (e.g., Shin Etsu SCR1011 or Shin Etsu SCR1016) using sufficient stirring to ensure good dispersion within the encapsulating polymer. The encapsulant mixture can then be transferred to a well in an LED chip and cured under an inert atmosphere using standard conditions for the LED encapsulant used.

Example 4

Reverse Emulsion Synthesis to Form Core/Shell Structured Silica Beads with Embedded Quantum Dots A solution of InP/ZnS core/shell quantum dots (containing 70 mg of inorganic material) was subjected to evaporation to remove most of the quantum dot solvent, Which in this case was toluene, and then mixed with silane monomers (e.g., 0.1 mL of 3-(trimethoxysilyl)propylmethacrylate (TMOPMA) and 0.5 mL of tetramethoxy silane (TEOS)) until a clear solution was obtained.

10 mL of degassed cyclohexane/Igepal™ CO-520 (CO-520 is $C_9H_{19}$-Ph-$(OCH_2CH_2)_n$—OH where n 5) (18 mL/1.35 g) was prepared in a 50 mL flask and 0.1 mL of 4% $NH_4OH$ injected to form a stable reverse emulsion.

The QD/silane mixture was then injected into the cyclohexane/CO-520/$NH_4OH$. The mixture was stirred at 500 rpm under $N_2$ overnight.

After 4 hours, another 0.5 mL of TEOS was injected into the reaction flask and the solution stirred overnight. The next day, another 0.1 mL of 4% $NH_4OH$ was injected into the flask and stirred for 3 hours. Silica heads containing the QDs with a further outermost silica layer were collected by centrifugation and washed with cyclohexane twice. The resulting sediment was then dried under vacuum.

Quantum Dot-Bead LED Fabrication

Quantum dot-containing core/shell structured silica microbeads prepared as described above can be mixed with an LED encapsulant (e.g., Shin Etsu SCR1011 or Shin Etsu SCR1016) using sufficient stirring to ensure good dispersion within the encapsulating polymer. The encapsulant mixture can then be transferred to a well in an LED chip and cured under an inert atmosphere using standard conditions for the LED encapsulant used.

Example 5

Epoxy Encapsulation of Cadmium Free Quantum Dot-Polymer Samples

An aliquot of a sample of InP/ZnS (cadmium free) quantum dots dispersed in polycarbonate polymer beads (30 mg) was placed under vacuum (−30 Psi) in the antechamber of a glove box (20 min) then refilled with $N_{2(g)}$. The antechamber was evacuated (−30 Psi) and refilled with $N_{2(g)}$ twice more.

The quantum dot-polymer sample was transferred into the glove box and an epoxy polymer (e.g., Optocast™ 3553 from Electronic Materials, Inc., USA) (30-90 μL) added followed by homogenisation.

The sample was irradiated (Hg-lamp, 400 W, 5 min) to cure the epoxy polymer so as to provide a hard and brittle polymer, which was then ground into a fine powder to provide epoxy beads containing the InP/ZnS quantum dots.

Quantum Dot-Bead LED Fabrication

Quantum dot-containing epoxy microbeads prepared as described above can be mixed with an LED encapsulant (e.g., Shin Etsu SCR1011 or Shin Etsu SCR1016) using sufficient stirring to ensure good dispersion within the encapsulating polymer. The encapsulant mixture can then be transferred to a well in an LED chip and cured under an inert atmosphere using standard conditions for the LED encapsulant used.

Comparative Example

Two quantum dot-containing light-emitting, devices were fabricated to compare their performance. One of the devices included CdSe/ZnS core/shell quantum dots (prepared as in Synthetic Method 1) incorporated directly into a commercially available LED encapsulant in accordance with prior art methods. The other device included the same type of quantum dots (prepared as in Synthetic Method 1) but with the dots incorporated into polymer beads embedded into the LED encapsulant in accordance with embodiments of the present invention (prepared as in Example 1).

The CdSe/ZnS quantum dots used in the comparative tests were obtained from the same batch, produced as described above in Synthetic Method 1. To make the prior art device, the quantum dots were embedded directly into Shin Etsu SCR1011 silicone as the LED encapsulant resin using standard methods. To make the device according to an embodiment of the present invention, the quantum dots were first incorporated into methyl methacrylate/ethylene glycol dimethacrylate 50% cross-linked beads which were then embedded into Shin Etsu SCR1011 silicone LED encapsulant resin using the methodology described above in Example 1.

The prior art LED encapsulant mixture was transferred to a well in a blue emitting LED chip and cured under an inert atmosphere using standard conditions for the LED encapsulant used. A similar process was carried out to fabricate the device according to an embodiment of the present invention but using the LED encapsulant mixture containing the quantum dot-containing polymer beads (QD-beads). Post curing, the two light-emitting devices were tested with a forward current of 20 mA and then continuously powered at room temperature at 20 mA. Periodically the photometric properties of the light-emitting devices were measured while powered with a forward current of 20 mA.

Figure 9:
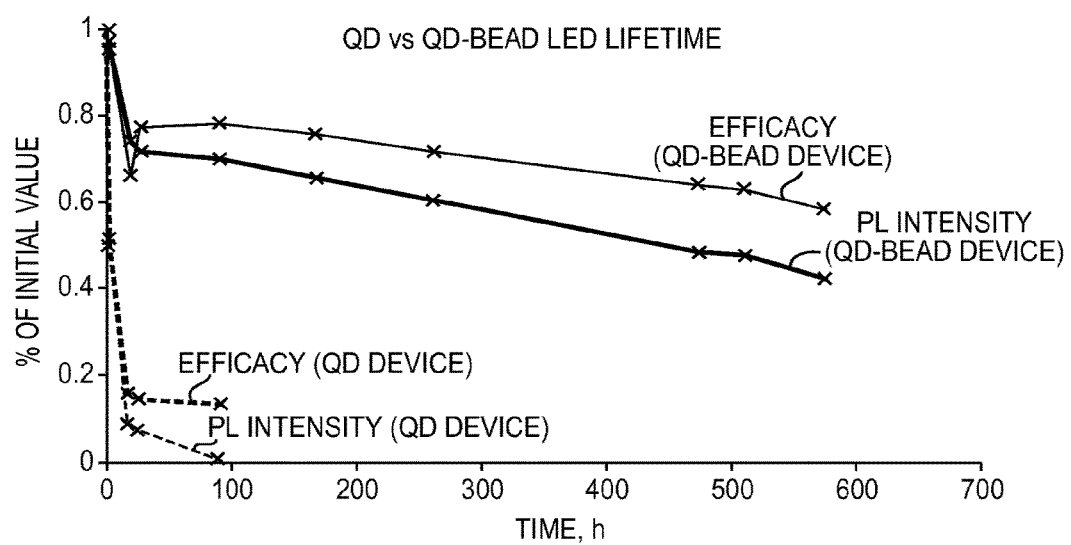
FIG. 9 is a plot of efficacy and quantum dot-photoluminescence intensity expressed as a percentage of the initial value versus time for the two devices described in the Comparative Example below.

The graph in FIG. 9 is a plot of efficacy and quantum dot-photoluminescence intensity expressed as a percentage of the initial value versus time. It should be noted that efficacy values for each device do not fall to zero since they include a contribution from the blue LED underneath the QD (or QD-bead) LED encapsulant composite. As such, efficacy does not fall to zero since the blue light from the LED is not diminished by the photodegradation of the QDs.

As can be seen from the results presented in FIG. 9, the QD-beads are more robust in the silicone LED encapsulant and provide enhanced light-emitting, device lifetimes, thereby demonstrating the improved performance of a light-emitting device according to embodiments of the present invention.

It will be seen that the techniques described herein provide a basis for improved production of nanoparticle materials. The terms and expressions employed herein are used as terms of description and not of limitation, and there is no intention in the use of such terms of and expressions of excluding any equivalents of the features shown and described or portions thereof. Instead, it is recognized that various modifications are possible within the scope of the invention claimed.

What is claimed is:

1. A light-emitting device comprising:
   a primary light source submerged in a formulation and in optical communication with the formulation,
   wherein the formulation comprises:
     a host encapsulation medium; and
     a plurality of discrete microbeads dispersed throughout the host encapsulation medium, each microbead comprising:
       an optically transparent medium; and
       a population of semiconductor nanoparticles incorporated within the optically transparent medium.

2. A light-emitting device according to claim 1, wherein the primary light source is selected from the group consisting of a light-emitting diode, a laser, an arc lamp, and a blackbody light source.

3. A light emitting device according to claim 1, wherein the optically transparent medium is any one of a resin, a polymer, a monolith, a glass, a sol gel, an epoxy, a silicone, and a (meth)acrylate.

4. A light emitting device according to claim 1, wherein the optically transparent medium is any one of a polystyrene microsphere having divinyl benzene and a thiol co-monomer, one or more silane monomers, and an epoxy polymer.

5. A light-emitting device according to claim 4, wherein the one or more silane monomers comprise 3-(trimethoxysilyl)propylmethacrylate or tetramethoxysilane.

6. A light-emitting device according to claim 1, wherein the semiconductor nanoparticles comprise one or more of CdS, CdSe, CdTe, ZnS, ZnSe, ZnTe, InP, InAs, InSb, AlP, AlS, AlAs, AlSb, GaN, GaP, GaAs, GaSb, PbS, PbSe, Si, Ge, MgS, MgSe, and MgTe.

7. A light-emitting device according to claim 1, wherein the host encapsulation medium comprises one or more of a silica glass, a silica gel, a siloxane, a sol gel, a hydrogel, an agarose, a cellulose, an epoxy, a polyether, a polyethylene, a polyvinyl, a poly-diacetylene, a polyphenylene-vinylene, a polystyrene, a polypyrrole, a polyimide, a polyimidazole, a polysulfone, a polythiophene, a polyphosphate, a poly(meth)acrylate, a polyacrylamide, a polypeptide, and a polysaccharide.

8. A light-emitting device comprising:
   a primary light source;
   a plurality of discrete microbeads, each microbead comprising an optically transparent medium and a population of nanoparticles incorporated into the optically transparent medium; and
   an encapsulation medium,
   wherein the primary light source is submerged in the encapsulation medium and the plurality of discrete microbeads are embedded within the encapsulation medium.

9. A light-emitting device according to claim 8, wherein the encapsulation medium comprises one or more of a silica glass, a silica gel, a siloxane, a sol gel, a hydrogel, an agarose, a cellulose, an epoxy, a polyether, a polyethylene, a polyvinyl, a poly-diacetylene, a polyphenylene-vinylene, a polystyrene, a polypyrrole, a polyimide, a polyimidazole, a polysulfone, a polythiophene, a polyphosphate, a poly(meth)acrylate, a polyacrylamide, a polypeptide, and a polysaccharide.

10. A light-emitting device according to claim 8, wherein the primary light source is selected from the group consisting of a light-emitting diode, a laser, an arc lamp, and a blackbody light source.

11. A light emitting device according to claim 8, wherein the optically transparent medium is any one of a polystyrene microsphere having divinyl benzene and a thiol co-monomer, one or more silane monomers, and an epoxy polymer.

12. A light emitting device according to claim 11, wherein the one or more silane monomers comprise 3-(trimethoxysilyl)propylmethacrylate or tetramethoxysilane.

* * * * *